United States Patent [19]
Reading

[11] Patent Number: 5,439,291
[45] Date of Patent: * Aug. 8, 1995

[54] METHOD AND APPARATUS FOR AC DIFFERENTIAL THERMAL ANALYSIS

[75] Inventor: Michael Reading, London, England

[73] Assignee: TA Instruments, Inc., New Castle, Del.

[ * ] Notice: The portion of the term of this patent subsequent to Apr. 6, 2010 has been disclaimed.

[21] Appl. No.: 171,656

[22] Filed: Dec. 22, 1993

Related U.S. Application Data

[63] Continuation-in-part of Ser. No. 60,214, May 7, 1993, Pat. No. 5,346,306, which is a continuation of Ser. No. 844,448, Mar. 2, 1992, Pat. No. 5,224,775.

[51] Int. Cl.$^6$ .................................... G01N 25/00
[52] U.S. Cl. .................................... 374/11; 374/33; 374/43
[58] Field of Search .................. 374/10, 11, 12, 13, 374/14, 16, 31, 33, 43

[56] References Cited

U.S. PATENT DOCUMENTS

| | | |
|---|---|---|
| 2,975,629 | 3/1961 | Herbert . |
| 3,263,484 | 8/1966 | Watson et al. . |
| 3,271,996 | 9/1966 | Paulik et al. . |
| 3,339,398 | 9/1967 | Barrall, II et al. . |
| 3,360,993 | 1/1968 | MacMillan . |
| 3,417,604 | 12/1968 | Bean et al. . |
| 3,527,081 | 9/1970 | Hill . |
| 3,732,722 | 5/1973 | Norem et al. . |
| 3,789,662 | 2/1974 | Zettler et al. . |
| 4,095,453 | 6/1978 | Woo . |
| 4,255,961 | 3/1981 | Biltonen et al. . |
| 4,350,446 | 9/1982 | Johnson . |
| 4,690,569 | 9/1987 | Veitch . |
| 4,783,174 | 11/1988 | Gmelin et al. . |
| 4,787,698 | 5/1988 | Wickramasinghe et al. . |
| 4,812,051 | 3/1989 | Paulik et al. . |
| 4,838,706 | 6/1989 | Coey et al. . |
| 4,840,496 | 6/1989 | Elleman et al. . |
| 4,848,921 | 7/1989 | Kunze . |
| 4,928,254 | 5/1990 | Knudsen et al. . |
| 5,046,858 | 10/1991 | Tucker . |
| 5,098,196 | 3/1992 | O'Neill . |
| 5,152,607 | 10/1992 | Ibar . |
| 5,224,775 | 7/1993 | Reading et al. . |
| 5,248,199 | 9/1993 | Reading . |

FOREIGN PATENT DOCUMENTS 0051266 5/1982 European Pat. Off. .
0380414 8/1990 European Pat. Off. .

OTHER PUBLICATIONS

N. Birge and S. Nagel, "Specific-Heat Spectroscopy of the Glass Transition, " Physical Review Letters, vol. 54, No. 25, Jun. 24,1985, pp.2674–2677.

N. Birge, "Specific-heat spectroscopy of glycerol and propylene glycol near the glass transition, " Physical Review B, vol. 34, No. 3, Aug. 1, 1986, pp. 1631–1642.

N. Birge and S. Nagel, "Wide-frequency specific heat spectrometer," Rev. Sci. Instrum., vol. 58, Aug. 1987, pp. 1464–1470.

G. S. Dixon, S. G. Black, C. T. Butler and A. K. Jain, "A Differential AC Calorimeter for Biophysical Studies,"Analytical Biochemistry, 121, 1982, pp. 55–61.

(List continued on next page.)

Primary Examiner—Thomas B. Will
Assistant Examiner—G. Bradley Bennett
Attorney, Agent, or Firm—Crowell & Moring

[57] ABSTRACT

The present invention is a modulated differential thermal analysis technique for determining the composition, phase, structure, identification, or other properties of a material that undergoes a transition as function of temperature or other driving variable. As applied to differential scanning calorimetric analysis (DSC), the preferred embodiment comprises (1) heating a sample of the material with a linear temperature ramp that is modulated with a sinusoidal heating rate oscillation; (2) simultaneously heating a reference at the same linear temperature ramp; (3) measuring the differential temperature of the sample and reference; and (4) deconvoluting the resultant heat flow signal into rapidly and non-rapidly reversible components.

92 Claims, 5 Drawing Sheets

OTHER PUBLICATIONS

K. Drong, I. Lamprecht and Th. Plesser, "Calorimetric Measurements of an Intermittency Phenomenon in Oscillating Glycolysis in Cell–Free Extracts from Yeast," Thermochimica Acta, vol. 151, 1989, pp. 69–81.

V. V. Filimonov, S. A. Potekhin, S. V. Matveev and P. L. Privalov, "Thermodynamic Analysis of Scanning Microcalorimetric Data," Biophysical Chemistry, vol. 87, 1987, pp. 87–96.

E. Freire and R. L. Biltonen, "Statistical Mechanical Deconvolution of Thermal Transitions in Macromolecules. I. Theory and Application to Homogeneous Systems," Biopolymers, vol. 17, pp. 463–479 (1978).

E. Freire, W. W. van Osdol, O. L. Mayorga and J. M. Sanchez-Ruiz, "Calorimetry Determined Dynamics of Complex Unfolding Transitions in Proteins," Annu. Rev. Biophys. Biophys. Chem. 1990. 19:159–88.

R. Garcia "Scanning Tunneling Microscopy in Biology: Changing the Pace," Microscopy and Analysis, Jul. 1991, pp. 27–29.

J. E. Graebner, "Modulated–bath calorimetry," Review of Scientific Instruments, Jun. 1989, pp. 1123–1128.

I. Hatta and A. Ikushima, "Studies on Phase Transitions by AC Calorimetry," Japanese Journal of Applied Physics, vol. 20, No. 11, Nov. 1981, pp. 1995–2011.

M. Hietschold, P. K. Hansma, A. L. Weisenhorn, "Scanning–Probe–Microscopy and Spectroscopy in Materials Science," Microscopy and Analysis, Sep. 1991, pp. 25–27.

S. Ideda and Y. Ishikawa, "Improvement of AC Calorimetry," Japanese Journal of Applied Physics, vol. 18, No. 7, Jul. 1979, pp. 1367–1372.

S. Imaizumi, T. Matsuda and I. Hatta, "Measurement of Dynamic Specific Heat Capacity of Lysozyme Crystals," Journal of the Physical Society of Japan, vol. 47, No. 5, Nov. 1979, pp. 1643–1646.

D. H. Jung, T. W. Kwon, D. J. Bae, I. K. Moon and Y. H. Jeong, "Fully automated dynamic colorimeter," Meas. Sci. Technol., vol. 3, 1992, pp. 475–484.

S. MacPherson, "Atomic Resolution," Laboratory News, Mar. 19, 1990.

O. L. Mayorga, W. V. van Osdol, J. L. Lacomba and E. Freire, "Frequency spectrum of enthalpy fluctuations associated with macromolecular transitions," Proc. Natl. Acad. Sci. U.S.A., vol. 85, Dec. 1988, pp. 9514–9518.

O. L. Mayorga and E. Freire, "Dynamic analysis of differential scanning calorimetry data," Biophysical Chemistry, vol. 87, 1987, pp. 87–96.

M. J. Miles, "The Application of STM/AFM To Biological Molecules," Microscopy and Analysis, Jul. 1990, pp. 7–9.

J. Mitchell, "DSC: A new design for evaluating the thermal behavior of materials," International Laboratory, Feb. 28, 1991, pp. 44–48.

R. Point, J. L. Petit and P. C. Gravelle, "Reconstruction of Thermokinetics from Calorimetric Data by Means of Numerical Inverse Filters," Journal of Thermal Analysis, vol. 17, 1979, pp. 383–393.

H. S. Rade, "Wechselstromkalorimetrie–ein empfindliches und kontinuierlich registrierendes Verfahren zur Messung spezifischer Warmen kleiner Proben," Feinwerktechnik & Messtechnik, Jul. 1977, pp. 223–226.

A. Rosencwaig, "Photoacoustic microscopy," International Laboratory, Sep./Oct. 1979, pp. 37–43.

P. Sullivan and G. Seidel, "Steady-state, ac–Temperature Calorimetry," Physical Review, vol. 173, No. 3, Sep. 15, 1968, pp. 679–685.

N. F. van Hulst and F. B. Segerink, "Optical Microscopy Beyond the Diffraction Limit," Microscopy and Analysis, Jan. 1992, pp. 21–23.

W. W. van Osdol, O. L. Mayorga and E. Freire, "Multifrequency calorimetry of the folding/unfolding transition of cytochrome c," Biophysical Journal, vol. 59, 1991, pp. 48–54.

W. W. Wendlandt, "Thermal Methods of Analysis," Dept. of Chemistry, University of Houston, Houston, Tex., Second Edition, 1974, pp. 193–212.

C. C. Williams and H. K. Wickramasinghe, "Photothermal Imaging with Sub-100-nm Spatial Resolution," Photoacoustic and Photothermal Phenomema Proceedings, pp. 364–368.

H. Yao and I. Hatta, "An ac Microcalorimetric Method for Precise Heat Capacity Measurement in a Small Amount of Liquid," Japanese Journal of Applied Physics, Jan. 1988, pp. 121–122.

Ulvac Sinku–Riko, Inc. product brochure ACC-1, "AC Calorimeter," publication date unknown, Catalog No. 8909-A13E/90.71000.

(List continued on next page.)

OTHER PUBLICATIONS

Ulvac Sinku-Riko, Inc. product brochure, "Thermal Constants Analyzer by AC Calorimetric Method," publication date unknown, Catalog No. 9010-P1TR1/90.10.3000.

Ulvac Sinku-Riko, Inc. product brochure ACC-VL1, "AC Calorimeter," publication date unknown, Catalog No. 9102-A24E.

Microscopy and Analysis, "Aris Scanning Tunneling Microscope," Jan. 1992.

Di product brochure, "Nanoscope II, Scanning Tunneling Microscope," Publication date unknown.

Struers product brochure, "Welcome to the World of Atoms, Tunnelscope 2400, Software Version 2.0," publication date unknown.

METHOD AND APPARATUS FOR AC DIFFERENTIAL THERMAL ANALYSIS

This application is a continuation-in-part of application Ser. No. 08/060,214, issued as U.S. Pat. No. 5,346,306 filed May 7, 1993 ("the parent application") which is a continuation of application Ser. No. 07/844,448 (the "grandparent application"), issued as U.S. Pat. No. 5,224,775, filed on Mar. 2, 1992, which are both incorporated by reference herein.

BACKGROUND

1. Field of the Invention

The present invention relates to thermal analytical techniques for determining the composition, phase, structure, or other properties of a sample of material.

2. Background of the Invention

Thermal analysis techniques generally comprise measuring a physical parameter as a function of the temperature of a material. Whenever a material undergoes a chemical transformation, a physical transformation, a phase change or another transition which affects the physical parameter being measured, the changes in that physical parameter may be interpreted to analyze the composition, structure, or thermal stability of the sample.

Traditional thermal analysis techniques can be improved by modulating the temperature of the sample and reference. Modulated differential thermal analysis techniques are described in the grandparent application, U.S. Pat. No. 5,224,775 to Reading et al. Modulated differential techniques improve the interpretation of differential scanning calorimetry ("DSC"; explained in more detail below) data by adding a sinusoidal temperature modulation to a linear DSC temperature ramp and deconvoluting the resultant heat flow signal into rapidly reversible and non-rapidly reversible components. In modulated DSC, just as in conventional DSC, the sample and reference materials are exposed to identical temperature programs.

DSC is a thermal analysis technique which measures the heat flows to/from a sample material and an inert reference material, as the sample and reference are exposed to the same controlled temperature. The difference in the heat flow measured for the sample and that measured for the reference is recorded, from which physical parameters of the sample are determined. See, e.g., W. W. Wendlandt, *Thermal Methods of Analysis*, 193–201 (1974).

Differential scanning calorimeters fall into two broad classes of instruments: heat flux DSC and power compensated DSC. Heat flux DSCs measure the dynamic temperature difference between a sample material and a reference material. Because the dynamic temperature difference is proportional to the total heat flow to/from the sample, the total heat flow to/from the sample is obtained from the dynamic temperature difference. See, e.g., U.S. Pat. No. 4,095,453 to Woo.

Power compensated differential scanning calorimeters control the total flow of heat to the sample material and reference material separately. The total flow of heat is controlled so as to maintain the temperature of the sample material at the temperature of the reference material during physical transformations in the sample material. The total heat flow to/from the sample material is calculated from the difference between the power supplied to the sample material and the power supplied to the reference material. See, e.g., U.S. Pat. No. 3,263,484 to Watson et al.

In traditional differential scanning calorimetry, the sample material and the reference material are simultaneously subjected to the regulated temperature environment. However, this is not essential to the operation of the calorimeter. Differential scanning calorimetry may be performed sequentially, by subjecting the sample material and the reference material to consecutive measurements, storing the results, and subsequently calculating the total heat flow to/from the sample. U.S. Pat. No. 4,848,921 to Kunze describes this technique in power compensation calorimeters. In principle, heat flux calorimeters could also measure the heat flow to/from the sample material and the reference material sequentially.

Differential Thermal Analysis ("DTA") is a thermal analysis technique similar to DSC, wherein the temperatures and heat flow associated with transitions in materials are measured as a function of temperature. However, unlike DSC, DTA results are semi-quantitative. DTA is generally carried out at higher temperatures than DSC.

Another common thermal analysis technique is AC calorimetry. AC calorimetry is a thermal analysis technique which measures the heat capacity or thermal diffusivity associated with chemical or physical transitions in materials as a function of time and temperature. In AC calorimetry the heat energy flow to/from the sample is controlled. The resulting temperature change of the sample is measured and recorded, from which the physical parameters of the sample are determined.

One AC calorimetry technique measures the heat diffusion through a material adiabatically. In this technique, a modulated heat source is applied to one surface of a thin flat sample of material, while the resultant temperature oscillations on the opposite surface are measured and recorded. The modulated heat source is typically chopped light, laser flash, or direct Joule-heating from a resistive heating element or furnace. A lock-in amplifier is typically used to detect the AC temperature being measured. See I. Hatta and A. J. Ikushima, Japanese Journal of Applied Physics, vol. 20, pp. 1995–2011 (1981); and S. Ikeda and Y. Ishikawa, Japanese Journal of Applied Physics, vol. 18, pp. 1367–1372 (1979). This technique does not measure the total heat flow to/from a sample, but instead measures the response at the rear face of a sample to an AC heat input at the front face of the sample. See Hatta et al., referenced above, FIG. 1a and pp. 1996–97. The heat capacity of the sample can then be calculated from the amplitudes of the sine components for the measured temperature oscillation and input heat signal. Id.

Another AC calorimetry technique measures the heat diffusion into a material nonadiabatically. In this technique a modulated heat source is applied to one surface of a sample, and the resultant temperature change at the point of heat application is measured and recorded. The modulated heat source is typically direct Joule-heating from a resistive heating element or furnace. The major benefits of this technique, as compared to adiabatic AC calorimetry, are reduced constraints on sample geometry and modulation frequency (which is limited only by the frequency of the heat source modulations. See N. O. Birge, Physical Review B, vol. 34, pp. 1631–1642 (1986); and D. H. Jung et al., Meas. Sci. Technol., vol. 3, pp. 475–476 (1992).

High resolution techniques are described in U.S. Pat. No. 5,165,792 to Crowe et al., which is incorporated by reference herein. High resolution techniques seek to improve the resolution of changes in a characterizing physical parameter by controlling the rate of sample heating during transitions as a function of the rate of change of the physical parameter. When non-differential thermal analysis techniques are used, the high resolution techniques are effective in improving resolution for many transitions. However, they usually reduce the sensitivity of transitions when applied to differential thermal analysis techniques. This is because, for most differential thermal analysis techniques, the magnitude of the differential physical parameter is a direct function of the heating rate. Reducing the heating rate during transitions causes the differential signal to change, which may alter or obscure the true differential signal resulting from the transition event. This obscuring of the physical parameter can reduce the utility of the high resolution techniques when applied to conventional differential thermal analysis techniques.

It is often advantageous to combine two or more characterizing physical parameters to more precisely characterize a material. However, when conventional thermal analysis techniques require multiple samples or multiple measurements, the accuracy of the results are affected by run-to-run and/or sample-to-sample variations. Furthermore, the additional experimental steps and apparatus required to perform separate measurements reduces laboratory productivity compared to a simultaneous measurement.

Conventional thermal analysis techniques, including DSC, DTA and AC calorimetry, are limited in their ability to separate non-reversible transitions caused by enthalpic processes (chemical or physical) from reversible transitions such as changes in the heat capacity of the sample. This is because the reversible and non-reversible processes often occur simultaneously, or severely overlapped in time and/or temperature.

In addition, both conventional and high resolution thermal analysis techniques cannot distinguish between rapidly reversible and non-rapidly reversible transitions within a single heating or cooling scan of the sample.

DEFINITIONS

"Transition" or "Transformation" as used herein, mean any type of physical or chemical transformation, phase change, or structural change in a material.

"Analyzing" as used herein with respect to materials means determining the composition, phase, structure, and/or identification of the material.

"Driving variable", as used herein, means the independent physical parameter, such as temperature, pressure, applied stress, or wavelength of incident radiation, that is being used to drive a material through a transition. For example, in thermal analysis techniques such as DSC, temperature is typically the driving variable.

"Characterizing differential physical parameter", as used herein, means the dependent differential physical parameter characterizing the sample, such as its heat flow, weight change, or change in dielectric or mechanical properties.

"Rapidly reversible" as used herein, means any portion of a signal, transition, or event which is a direct function of the rate of change of the driving variable. For example, the contribution to the total heat flow signal in a DSC attributable to the rate of change of temperature of the sample material is a rapidly reversible transition. In a DSC, for example, one of the contributions to the rapidly reversible portion of the total heat flow signal is the heat capacity of the sample material. Rapidly reversible processes include those processes which are thermodynamically reversible and have small kinetic time constants relative to the rate of change of the driving variable.

"Non-rapidly reversible" as used herein, means any portion of a signal, transition or event which is a direct function of the value of the driving variable. For example, the contribution to the total heat flow signal in a DSC attributable to the absolute temperature of the sample material is a non-rapidly reversible transition. This might be caused by a chemical or physical change taking place such as recrystallization. Non-rapidly reversible processes include those processes which are thermodynamically irreversible, as well as processes which are thermodynamically reversible, but which reverse very slowly relative to the rate of change of the driving variable due to the kinetic limitations of the process.

"Deconvolution", as used herein, means the process of separating the dependence of a characterizing physical parameter such as total heat flow on temperature into two or more component parts so that the component parts can be utilized or analyzed separately, or compared with each other. For example, the dependence of the total heat flow can be deconvoluted into rapidly reversible heat flow and non-rapidly reversible heat flow components.

"Signal baseline" as used herein, means that portion of a signal representing the value of a characterizing physical parameter obtained in a range in which there are no transitions or transformations.

"Sensitivity" of an analytical technique, as used herein, means the degree to which signals associated with transitions can be physically distinguished from the signal baseline in the analytical data produced by the technique. This quality of the analytical technique is most critical when the value of the driving variable is changing very slowly.

"Resolution" of an analytical technique, as used herein, means the degree to which signals associated with different transitions can be physically separated in the analytical data produced by the technique. This quality of the analytical technique is most critical when multiple transitions occur at closely spaced values of the driving variable.

"Moving averaged", is a data smoothing technique that can be applied to data collected as discrete data points at uniform increments, comprising averaging the raw data over a window of n data points to obtain a single smoothed data point, incrementing the window by one data point, and repeating the process until all the data has been averaged. Thus the first n raw data points, data points i=1, ... n, are averaged to calculate the first smoothed data point, data points i=2, ... n+1, are averaged to produce the second data point, etc.

A "pulse wave" is a wave of spikes or impulse functions occurring at regular intervals. As applied to thermal analysis techniques, a pulse wave could be produced by bursts of instantaneous energy, e.g., from a laser, at regular intervals. The key characteristic of a pulse wave is that the duration of the energy burst is short compared to the duration of its effect.

"Reference material," as used herein, includes both a material being used as a reference in the conventional sense, and nothing being used as the reference, e.g., if a reference pan is used, using an empty reference pan.

When nothing is being used as the reference, "placing a reference material at the reference position," means ensuring that the reference position does not have any material thereon, i.e., removing any material from the reference position, if necessary. When a material is actually being used as a reference, "placing a reference material at the reference position," includes removing any material from the reference position, if necessary.

When nothing is being used as the reference, "placing a reference material at the sample position," means ensuring that the sample position does not have any material thereon, i.e., removing any material from the sample position, if necessary. When a material is actually being used as a reference material, "placing a reference material at the sample position," includes removing any material from the sample position, if necessary.

"Placing a sample at the sample position," as used herein, includes removing any material from the sample position, if necessary.

SUMMARY OF THE INVENTION

The present invention is similar to Modulated DSC. However, the present invention differs from Modulated DSC in that the sample and reference materials are exposed to different temperature programs, the difference being the oscillating component of the temperature program. Thus, in the present invention, the sample material is exposed to both an oscillating heating rate component and a constant heating rate component, whereas the reference material is exposed to only the constant heating rate component.

In a first preferred embodiment of the present invention, a heat flux DSC apparatus is used to measure simultaneously the differential heat flow to/from the sample material, and the heat capacity of the sample material. The temperature of the DSC enclosure is controlled at the desired heating rate while a small controlled oscillating heat flow is applied to only the sample material. The average differential heat flow to the reference and sample materials, the average sample temperature, and the sample temperature amplitude are then recorded. The heat capacity of the sample material is then calculated by:

$$C_p = \frac{Q_{ac}}{2\pi \times f \times T_{ac}}$$

where:
- $C_o$ = heat capacity
- $Q_{ac}$ = amplitude of the heat flow oscillation
- $T_{ac}$ = amplitude of the sample temperature oscillation
- $f$ = frequency of the heat flow oscillation.

The rapidly reversible component of the total heat flow is computed as the heat capacity ($C_p$) multiplied by the underlying heating rate. The non-rapidly reversible component of heat flow is computed as the average differential total heat flow minus the rapidly reversible heat flow.

In a second preferred embodiment of the present invention, a power compensation DSC apparatus is used to measure simultaneously the differential heat flow to/from the sample material, and the heat capacity of the sample material. The temperature of the reference and sample is controlled at the desired heating rate by applying heat energy to both the reference and sample materials such that the average difference between the reference temperature, the sample temperature and the set point temperature is driven to zero. At the same time, a small controlled oscillating heat flow is added to only the sample material. The average differential heat flow to the reference and sample materials, the average sample temperature, and the sample temperature amplitude are then recorded. The heat capacity of the sample material, and the rapidly reversible and non-rapidly reversible components of heat flow, are then calculated as in the first preferred embodiment.

In a third preferred embodiment of the present invention, a single position/single furnace heat flux DSC apparatus is used to measure simultaneously the differential heat flow to/from the sample material, and the heat capacity of the sample material. First, the temperature of the heat flux DSC enclosure containing only the reference material is controlled at the desired heating rate as the temperature of the furnace and the temperature of the reference material are recorded. The sample is then exposed, in the same enclosure, to the same furnace average temperature heating profile as that stored for the reference material, but with a small temperature oscillation due to a small controlled oscillating heat flow that is applied to the sample. The average differential total heat flow to the sample with respect to the reference, the average sample temperature, and the sample temperature amplitude are then recorded. The heat capacity of the sample material, and the rapidly reversible and non-rapidly reversible components of the total heat flow, are then calculated as in the first preferred embodiment.

In a fourth preferred embodiment of the present invention, a single position/single furnace power compensation DSC apparatus is used to measure simultaneously the differential heat flow to/from the sample material, and the heat capacity of the sample material. First, the temperature of the reference material is controlled at the desired heating rate as the amount of heat energy supplied to the reference and the reference temperature are stored. The sample is then exposed, in the same enclosure, to the heat energy as recorded for the reference, such that supplemental heat energy is supplied to the sample to compensate for any average variation in temperature between the sample temperature and stored reference temperature. At the same time, a small controlled oscillating heat flow is added only to the sample material. The average differential heat flow to the reference and sample materials, the average sample temperature, and the sample temperature amplitude are then recorded. The heat capacity of the sample material, and the rapidly reversible and non-rapidly reversible components of heat flow, are then calculated as in the first preferred embodiment.

In each of the preferred embodiments, the oscillating heat flow is added to only the sample material. The oscillating heat flow may be generated by a number of different means. In the embodiments employing power compensation, the preferred method for adding the oscillating heat flow to the sample material is to oscillate the power to the sample heater. In the embodiment employing heat flux within a dual position calorimeter, the preferred method of adding oscillating heat flow to the sample material is to expose the surface of the sample material to a controlled source of chopped incident radiation. In the embodiment employing heat flux within a single position calorimeter, the preferred method of adding oscillating heat flow to the sample material is to vary the furnace temperature in an oscillating fashion from the linear heating program. However, it should be noted that in all of the preferred embodiments other means may be employed to produce an oscillating heat flow into (or out of) the sample material. These include, but are not limited to, Peltier devices, resistive heating elements, fluid baths and gas heat exchangers.

In each of the preferred embodiments, the oscillating heat flow may be characterized as having a wave shape. The preferred wave shape is a sine wave. However, other heat flow wave shapes may be employed including square waves, sawtooth waves, pulse waves, polynomial waves or combinations thereof.

A first object of the present invention is to provide a method for controlling the temperature in differential analysis techniques to substantially improve the resolution of transitions through the use of variable heating rates.

A second object of the present invention is to provide a temperature control method for differential thermal analysis techniques which achieves substantially improved resolution of transitions through the use of variable heating rate heating techniques.

A third object of the present invention is to separate the characterizing differential physical parameter into rapidly reversible and non-rapidly reversible components.

A fourth object of the present invention is to provide the analyst with a method of adjusting the amount of separation between rapidly reversible and non-rapidly reversible transitions.

A fifth object of the present invention is to improve the sensitivity of differential analysis techniques.

A sixth object of the present invention is to provide the analyst with an alternate method for studying the kinetic properties of chemical reactions.

A seventh object of the present invention is to obtain more accurate transition temperatures.

An eighth object of the present invention is to simplify the interpretation of differential thermal analysis data by more sharply defining the temperatures at which transitions occur.

A ninth object of the present invention is to isolate signal changes so that they can be more easily measured, integrated, compared with other results, and interpreted.

These and other objects of the present invention are described in greater detail in the detailed description of the invention, the appended drawings and the attached claims.

DESCRIPTION OF PREFERRED EMBODIMENTS OF THE INVENTION

The following detailed description of the present invention applies specifically to heat flux differential scanning calorimetry and to power compensation differential scanning calorimetry, in which temperature is the driving variable and heat flow is the characterizing differential physical parameter. However, although the present invention is described as it is applied to differential scanning calorimetric analysis, it should be understood that the present invention could be used with any differential thermal analysis method including, for example, pressure DSC, pressure DTA, simultaneous DTA/TGA, and differential photocalorimetry (DPC).

Figure 1:
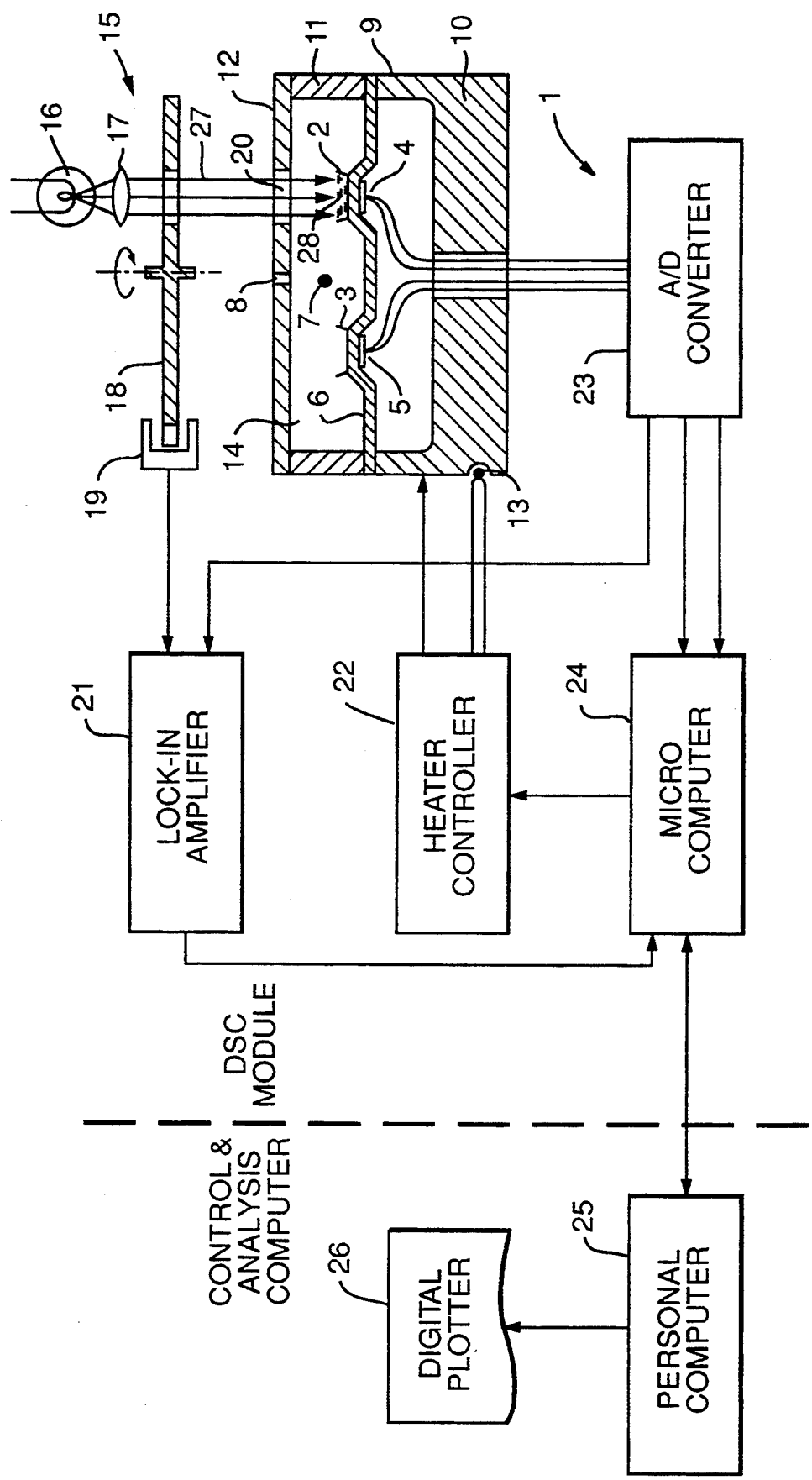
FIG. 1 is a schematic block diagram of a single-scan heat flux differential scanning calorimeter implementing the first preferred embodiment of the present invention.

FIG. 1 is a schematic representation of the first preferred embodiment of the present invention comprising a single-scan heat flux differential scanning calorimeter 1 comprising: sample pan 2; reference pan 3; sample temperature thermocouple 4; reference temperature thermocouple 5; thermoelectric disc 6; purge gas inlet 7; purge gas outlet 8; electric furnace 9 comprising silver block heater 10, silver ring 11, silver lid 12, and heater thermocouple 13; furnace chamber 14; heater controller 22; analog-to-digital ("A/D") converter 23; and microcomputer 24.

FIG. 1 also shows radiation source 15 comprising: halogen lamp 16; focusing lens 17; optical chopper 18; photo-interrupter 19; and lock-in amplifier 21; personal computer 25 and digital plotter 26. The differential scanning calorimeter measures the heat flow difference between sample pan 2 and reference pan 3 which are supported on thermoelectric disc 6 inside closed furnace chamber 14. Thermoelectric disc 6 serves as the major heat flow path for transferring heat from furnace 9 to sample pan 2 and reference pan 3. Thermoelectric disc 6 is also the common material for the differential thermocouple, for measuring the temperature difference between the sample and reference pans. For example, if sample thermocouple 4 and reference thermocouple 5 are chromel-alumel thermocouples, and thermoelectric disc 6 is made from constantan, the differential thermocouple is formed by the chromel wire of sample thermocouple 4, constantan thermolectric disc 6, and the chromel wire from reference thermocouple 5.

Microcomputer 17 receives differential temperature and sample temperature from sample thermocouple 4 and reference thermocouple 5 via analog-to-digital converter 23. Microcomputer 24 also controls the temperature of the furnace 9 by controlling the power to the furnace using heater controller 22. AC radiation source 15 exposes the top surface of sample 28 to chopped radiation 27 from halogen lamp 16 through aperture 20 in silver lid 12. Aperture 20 could be a hole in silver lid 12, or a window, e.q., a quartz window, in silver lid 12. In some cases, it might be advantageous to provide an aperture above reference pan 3 to match aperture 20 above sample pan 2, and thus to minimize any differences between the sample and reference sides of the apparatus. The radiation from halogen lamp 16 is focused into a parallel beam by lens 17 and chopped at the desired frequency by optical chopper 18. The AC temperature response of sample 28 to the chopped radiation source 27 is measured by lock-in amplifier 21 using the chopped synchronization signal from photointerrupter 19 and the sample temperature from A/D converter 23.

FIG. 1 also shows personal computer 25 and digital plotter 26. In the first preferred embodiment of the present invention, the temperature of the furnace and speed of the chopper are controlled by the microcomputer in accordance with the steps outlined below. However, the present invention can be practiced using any combination of computers, hardware and operator control. Personal computer 25 and digital plotter 26 are used to store and analyze the data, and to store, display and plot the analytical results. A purge gas is usually introduced via purge gas inlet 7. As is known in the field, depending upon the analysis, the purge gas can be a gas that reacts with constituents of the sample being analyzed, or it can be an inert gas, i.e., a gas that does not react with the sample used to prevent reactions with air. Typical purge gases include dry air, oxygen, nitrogen, argon, helium, carbon monoxide and carbon dioxide.

Figure 2:
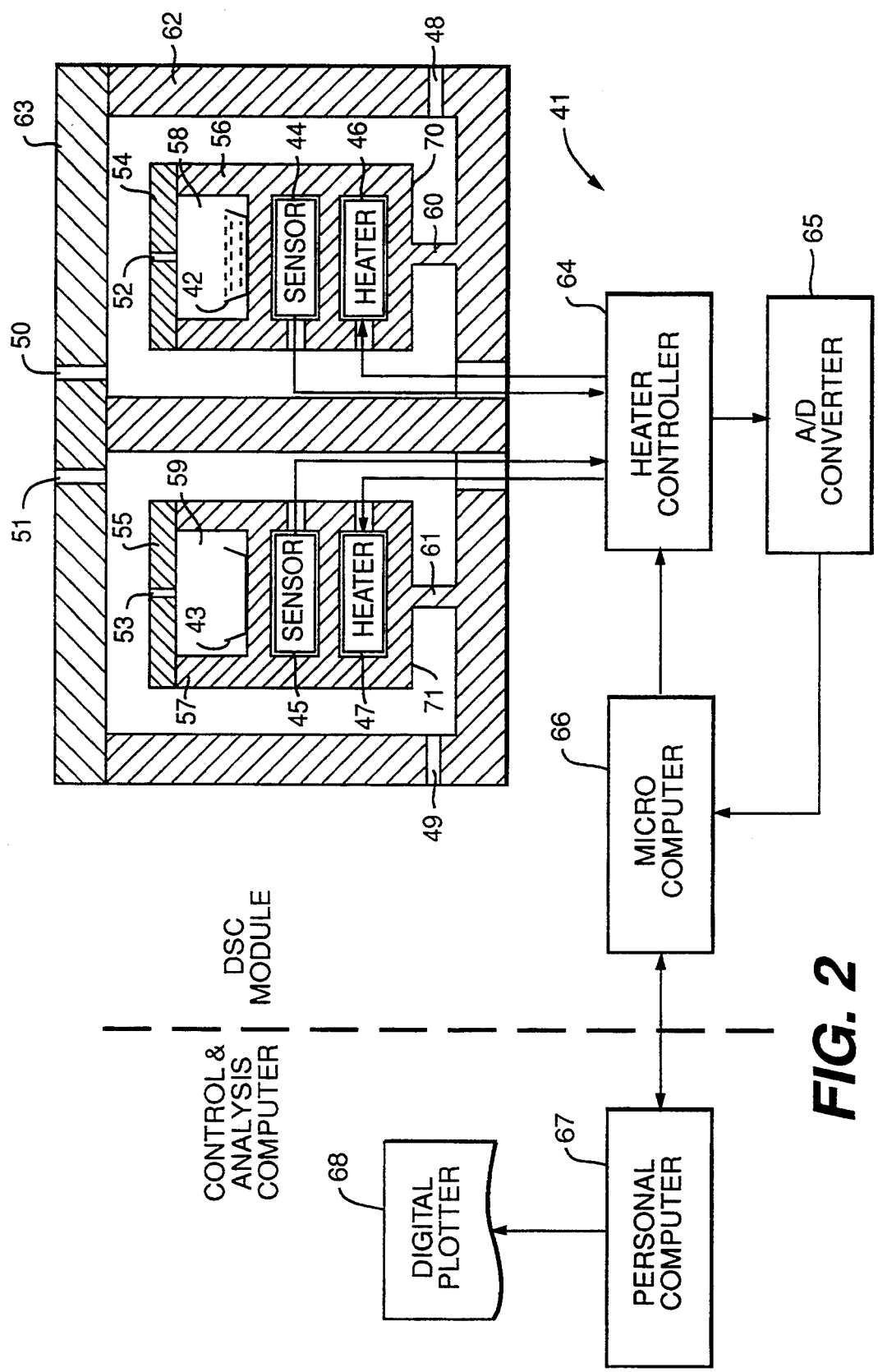
FIG. 2 is a schematic block diagram of a single-scan power compensated differential scanning calorimeter implementing the second preferred embodiment of the present invention.

FIG. 2 is a schematic representation of the second preferred embodiment of the present invention comprising a single-scan power compensation differential scanning calorimeter 41 comprising: sample furnace 70 comprising platinum enclosure 56, platinum lid 54, purge port 52, sample pan 42, sample temperature sensor 44, heater 46, furnace chamber 58, and furnace support 60; reference furnace 71 comprising platinum enclosure 57, platinum lid 55, purge port 53, reference pan 43, reference temperature sensor 45, heater 47, furnace chamber 59, and furnace support 61; heat sink 62; heat sink lid 63; purge gas inlets 48 and 49; purge gas outlets 50 and 51; heater controller 64; analog-to-digital converter 65; and microcomputer 66.

FIG. 2 also shows personal computer 67 and digital plotter 68. The differential scanning calorimeter measures the heat flow difference between sample pan 42 and reference pan 43 by measuring the differential power supplied to sample heater 46 and to reference heater 47 as sample sensor 44 and reference sensor 45 are maintained at the same average temperature. Microcomputer 66 receives power measurement from heater controller 64 and sample temperature measurement from AD converter 65. Microcomputer 66 also controls the temperature of furnaces 70 and 71 by controlling the power to each furnace using heater controller 64. Microcomputer 66 measures the heat capacity of sample 42 by applying a small sinusoidal power oscillation to heater 46 and measuring the resultant oscillation in sample temperature via sensor 44.

FIG. 2 also shows personal computer 67 and digital plotter 68. In the second preferred embodiment of the present invention, the temperature of the furnace and the amplitude and frequency of the heater power oscillation are controlled by the microcomputer in accordance with the steps outlined below. However, the present invention can be practiced using any combination of computers, hardware and operator control. Personal computer 67 and digital plotter 68 are used to store and analyze data and to store, display and plot the analytical results. A purge gas is usually introduced via purge gas inlets 48 and 49. Depending upon the analysis, the purge gas can be a gas that reacts with constituents of the sample being analyzed, or it can be an inert gas, i.e., a gas that does not react with the sample used to prevent reactions with air. Typical purge gases include dry air, oxygen, nitrogen, argon, helium, carbon monoxide and carbon dioxide.

Figure 3A:
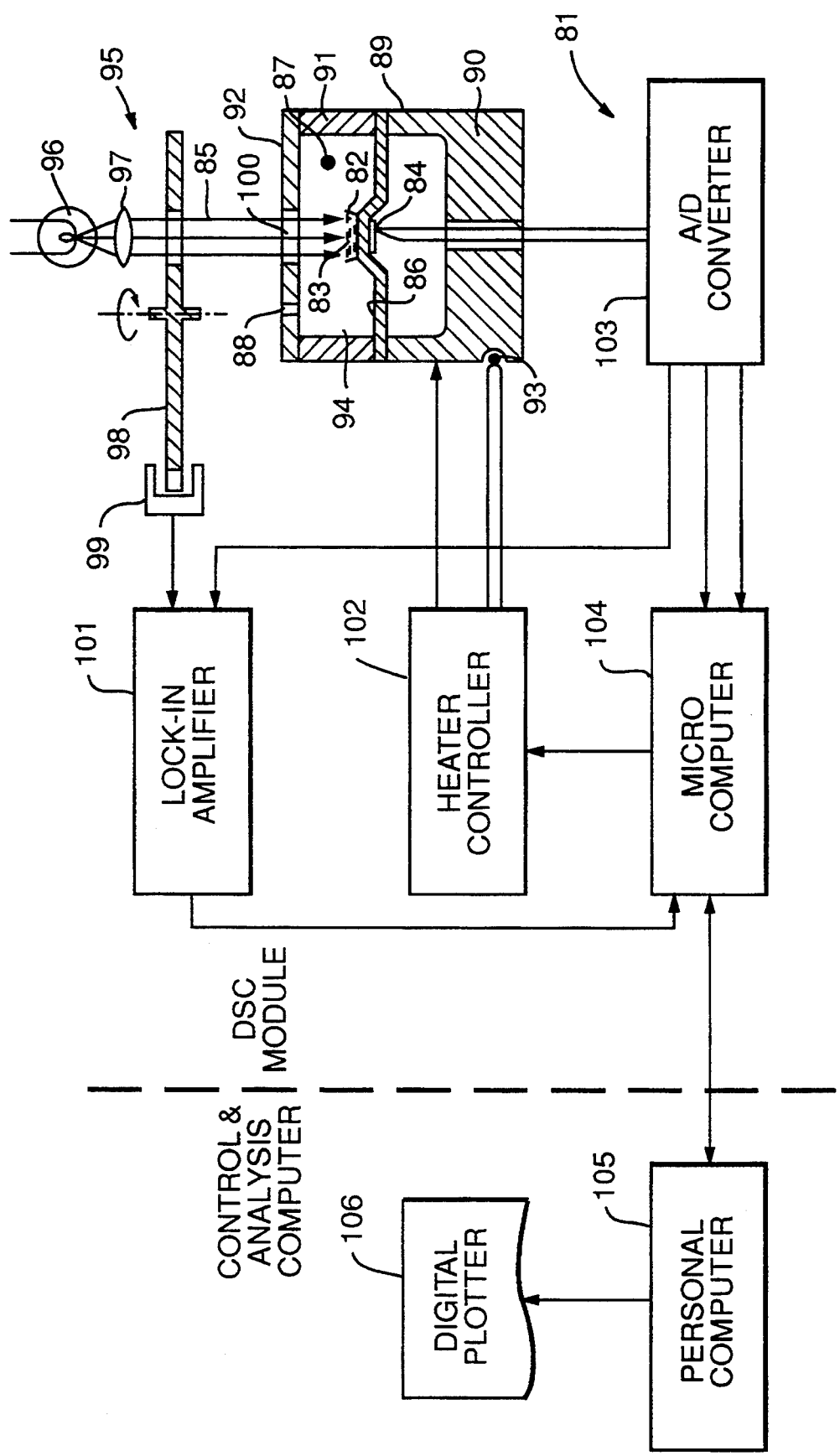
FIGS. 3A and 3B are schematic block diagrams of dual-scan heat flux differential scanning calorimeters, showing two alternative instruments for implementing the third preferred embodiment of the present invention.
Figure 3B:
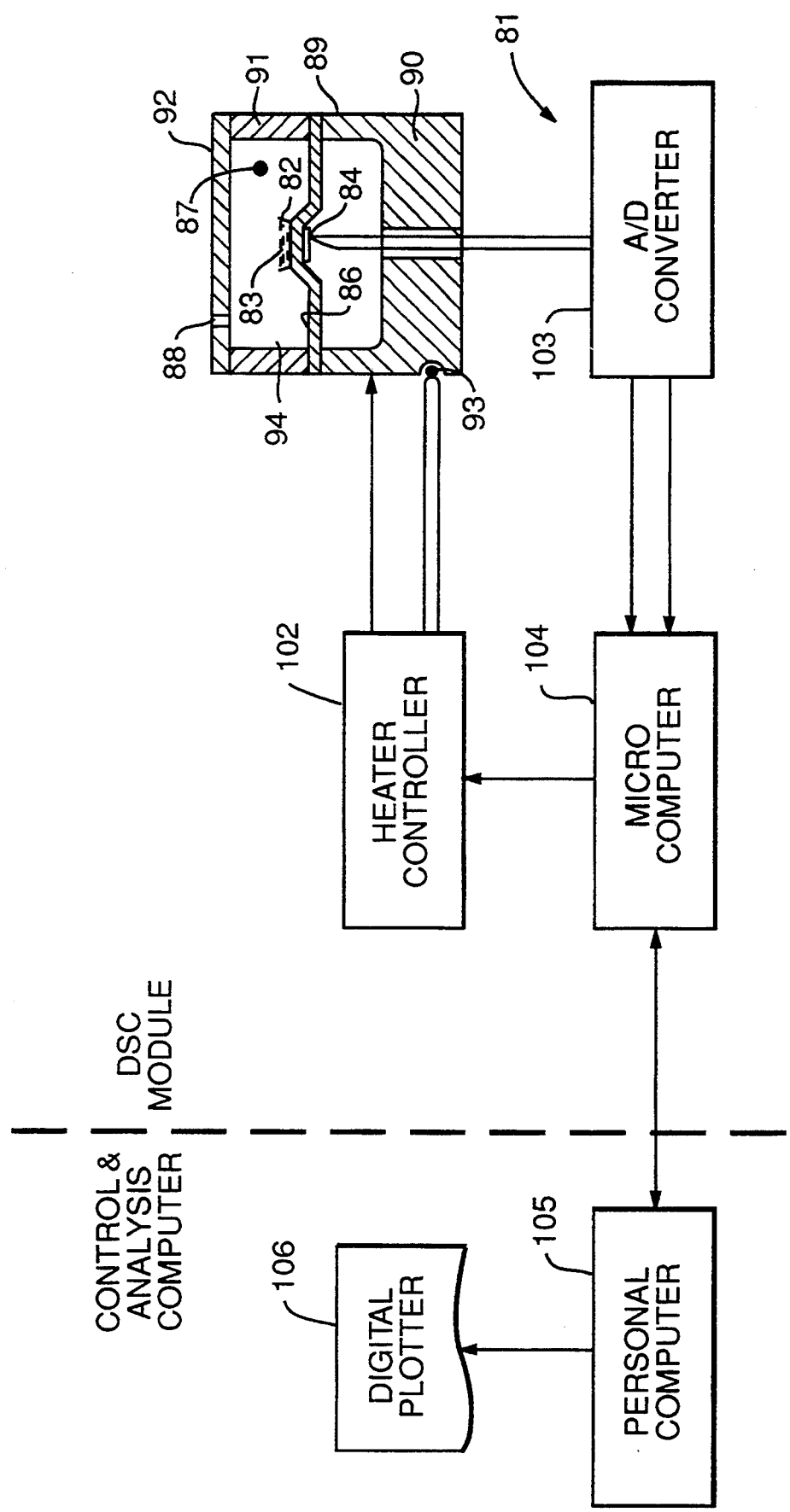

FIGS. 3A and 3B are a schematic representation of "optical chopper" and "modulated furnace," respectively, alternatives for the third preferred embodiment of the present invention. Both alternatives comprise a dual-scan heat flux differential scanning calorimeter 81 comprising: pan 82; sample 83; thermocouple 84; thermoelectric disc 86; purge gas inlet 87; purge gas outlet 88; electric furnace 89 comprising silver block heater 90, silver ring 91, silver lid 92, and heater thermocouple 93; furnace chamber 94; heater controller 102; analog-to-digital converter 103; and microcomputer 104.

FIG. 3A also shows AC radiation source 95 comprising: halogen lamp 96; focusing lens 97; optical chopper 98; photointerrupter 99; and lock-in amplifier 101. FIG. 3A also shows personal computer 105 and digital plotter 106. The differential scanning calorimeter 81 measures the heat flow difference between a reference material and a sample material by first placing a reference material in pan 82, scanning the temperature of the furnace, and recording the pan temperature as the reference temperature, using thermocouple 84, A/D converter 103 and microcomputer 104. Alternatively, the reference scan may be obtained without putting any reference material in pan 82, i.e., with an empty pan. In either case, the temperature of the furnace is scanned, and the temperature of pan 82 is recorded as the sample temperature. The previously recorded reference temperature is subtracted from the measured pan temperature, and the difference is converted to differential heat flow. Halogen lamp 96 is turned off during the reference scan. During each scan pan 82 is supported on a thermoelectric disc 86 inside a closed furnace chamber 94. Thermoelectric disc 86 serves as the major heat flow path for transferring heat from furnace 89 to pan 82. Microcomputer 104 receives temperature from thermocouple 84 via analog-to-digital converter 103. Microcomputer 104 also controls the temperature of the furnace 89 by controlling the power to the furnace using heater controller 102.

During a sample scan, AC radiation source 95 exposes the top surface of the sample 83 to chopped radiation 85 from halogen lamp 96 through aperture 100 in silver lid 92. Aperture 20 could be a hole or a window. The radiation from halogen lamp 96 is focused into a parallel beam by lens 97 and chopped at the desired frequency by optical chopper 98.

The AC temperature response of sample 83 to chopped radiation 85 is measured by lock-in amplifier 101 using the chopper synchronization signal from photointerrupter 99 and the sample temperature from A/D converter 103. FIG. 3A also shows personal computer 105 and digital plotter 106. In the third preferred embodiment of the present invention, the temperature of the furnace and speed of the chopper are controlled by microcomputer 104. However, the present invention can be practiced using any combination of computers, hardware and operator control. Personal computer 105 and digital plotter 106 are used to analyze, store, display and plot the analytical results. A purge gas is usually introduced via purge gas inlet 87. Depending upon the analysis, the purge gas can be a gas that reacts with constituents of the sample being analyzed, or it can be an inert gas, i.e., a gas that does not react with the sample used to prevent reactions with air. Typical purge gases include dry air, oxygen, nitrogen, argon, helium, carbon monoxide and carbon dioxide.

FIG. 3B is similar to FIG. 3A, but does not include a source of chopped radiation. Instead, the temperature of pan 82 is modulated during the sample scan by modulating the temperature of furnace 89, using heater controller 102.

Figure 4:
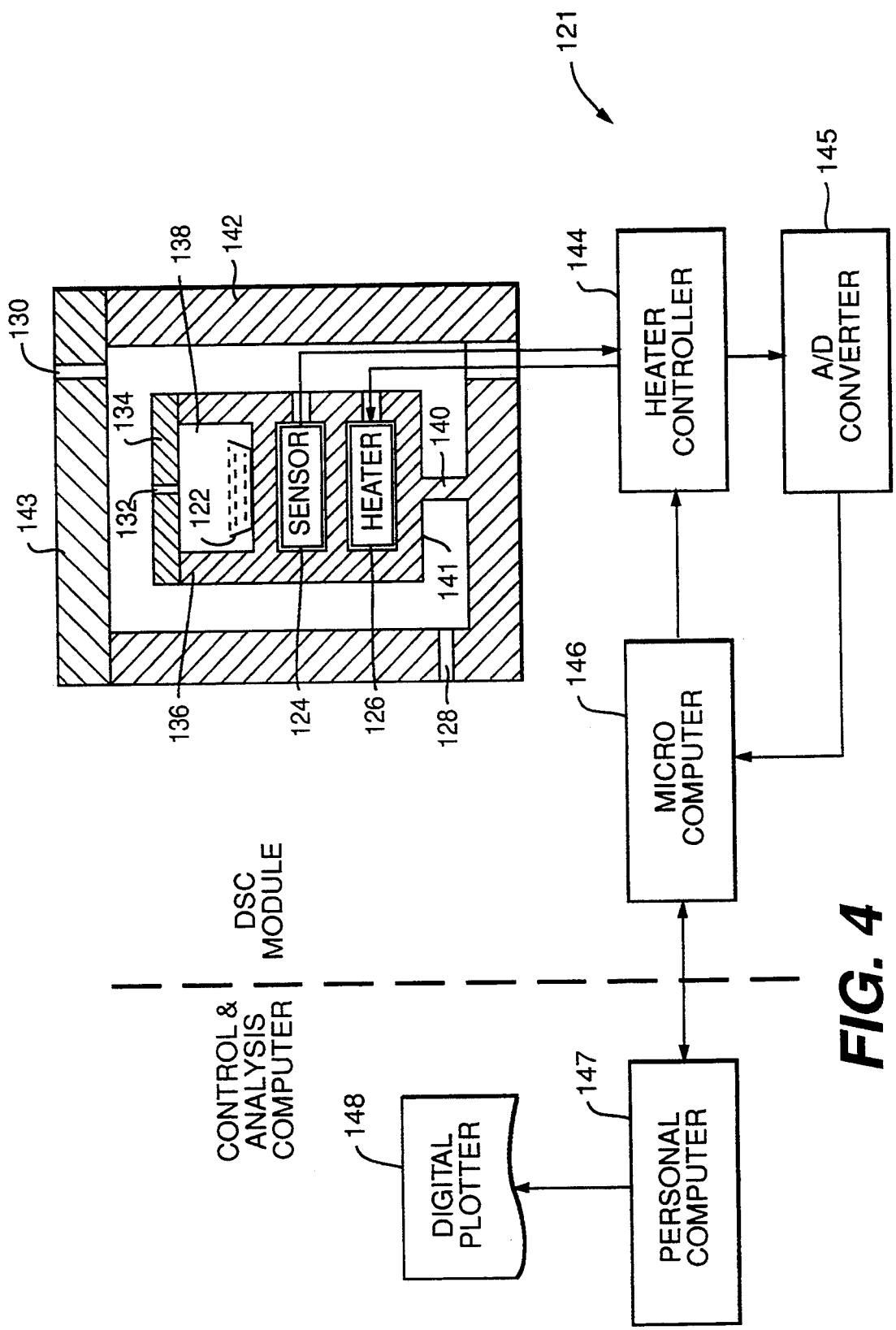
FIG. 4 is a schematic block diagram of a dual-scan power compensated differential scanning calorimeter implementing the fourth preferred embodiment of the present invention.

FIG. 4 is a dual-scan power compensation device where the reference and sample runs are made separately, as described in U.S. Pat. No. 4,848,921 to Kunze, which is incorporated by reference herein. The calculations are the same as for the second embodiment. FIG. 4 shows dual-scan power compensation differential scanning calorimeter 121, comprising furnace 141 comprising platinum enclosure 136, platinum lid 134; purge port 132, pan 122, temperature sensor 124, heater 126, furnace chamber 138, and furnace support 140; purge gas outlet 130; heat sink lid 143; purge gas inlet 128; heater controller 144; A/D converter 145; and microcomputer 146.

FIG. 4 also shows personal computer 147 and digital plotter 168. These components perform the same functions as the corresponding components of the second embodiment, shown on FIG. 2, except that the reference and sample data are obtained sequentially.

In both heat flux and power compensation instruments the applied heat energy absorbed by the sample from the AC radiation source must be added to the total heat flow to the sample. In the case of the heat flux device the power applied must be "known" from calibration or separate measurement since the DSC cannot measure it. One way to measure the energy would be to run a scan of an inert sample of known heat capacity ($C_p$) and light absorption similar to the light absorption of the sample material. Using the measured temperature amplitude ($T_{ac}$) and the selected frequency ($f$) the heat flow over one cycle (Q) due to the radiant energy should be:

$$Q = C_p \times T_{ac} \times 2\pi \times f$$

The heat flow from the AC radiation source is then added to the moving average of the heat flow over one light exposure cycle.

The $C_p$ of the sample material can now be determined and used to create the rapidly reversible component of heat flow signal ($C_p \times$ underlying heating rate) and the non-rapidly reversible component of heat flow (total heat flow minus the rapidly reversible heat flow).

In the case of the power compensation instruments, the power applied to the sample, and hence the heat flow, is always known due to direct measurement. Therefore, the heat capacity of the sample material is directly calculated by:

$$C_p = \frac{Q_{ac}}{T_{ac} \times 2\pi \times f}$$

The rapidly reversing component of heat flow is then $C_p$ times the underlying heating rate of the DSC. The total DSC heat flow is the average over one cycle of the applied heat flows (compensating plus oscillating) and all other results are as in the case of the heat flux device.

FURTHER IMPROVEMENTS

The embodiments shown in FIGS. 1 and 3A could be modified by applying a uniform light-absorbing material over the sample material and the reference pan (or reference material, when a reference material is used). The use of the light absorbing material could improve the calibration of the heat supplied by the optical radiation.

Additional calorimetric information may also be obtained by measuring the lag in phase between the modulation of the furnace temperature (FIG. 3B) or the modulation of the optical radiation (FIGS. 1 and 3A) and the temperature of the sample.

The foregoing disclosure of embodiments of the present invention has been presented for purposes of illustration and description. It is not intended to be exhaustive or to limit the invention to the precise forms disclosed. Many variations and modifications of the embodiments described herein will be obvious to one of ordinary skill in the art in light of the above disclosure. The scope of the invention is to be defined only by the claims appended hereto, and by their equivalents.

What is claimed is:

1. A method for analyzing a material comprising the steps of:
    (a) providing a heat flux differential scanning calorimeter having a sample position and a reference position, said differential scanning calorimeter having means for measuring the differential heat flow to the sample position with respect to the reference position;
    (b) selecting an underlying heating rate;
    (c) selecting a modulation function characterized by a modulation frequency and a modulation amplitude;
    (d) placing a sample of the material on the sample position of the differential scanning calorimeter and placing a reference material on the reference position of the differential scanning calorimeter;
    (e) varying the temperature of the sample position such that the average temperature of the sample position increases at the underlying heating rate, and applying an oscillating heat flow to the sample position, said heat flow oscillating according to the selected modulation function;
    (f) varying the temperature of the reference position at the selected underlying heating rate;
    (g) measuring the temperature of the sample position and measuring a differential signal representative of the total heat flow to the sample position with respect to the reference position; and
    (h) deconvoluting the differential signal representative of the total heat flow to the sample position with respect to the reference position to compute at least one deconvoluted signal.

2. The method of claim 1, wherein the step of deconvoluting the differential signal representative of the total heat flow comprises deconvoluting the differential signal representative of the total heat flow into a signal representative of the rapidly reversible heat flow and the non-rapidly reversible heat flow.

3. The method of claim 2, further comprising the step of controlling the underlying heating rate according to the signal representative of the rapidly reversible heat flow.

4. The method of claim 2, further comprising the step of controlling the underlying heating rate according to the signal representative of the non-rapidly reversible heat flow.

5. The method of claim 2, wherein the modulation function is a sinusoidal function.

6. The method of claim 2, wherein the modulation function is selected from the group of modulation functions consisting of square waves, sawtooth waves, triangular waves, pulse waves, polynomial waves and combinations thereof.

7. The method of claim 2, wherein the modulation frequency is selected to improve the separation between the signal representative of the rapidly reversible heat flow and the signal representative of the non-rapidly reversible heat flow.

8. The method of claim 2, wherein the modulation amplitude is selected to improve the separation between the signal representative of the rapidly reversible heat flow and the signal representative of the non-rapidly reversible heat flow.

9. The method of claim 1, wherein the step of deconvoluting the differential signal representative of the total heat flow comprises deconvoluting the differential signal representative of the total heat flow into a signal representative of the rapidly reversible heat flow and a signal representative of the non-rapidly reversible heat flow using a discrete Fourier transform.

10. The method of claim 1, wherein the step of deconvoluting the differential signal representative of the total heat flow comprises deconvoluting the differential signal representative of the total heat flow into a signal representative of the rapidly reversible heat flow and a signal representative of the non-rapidly reversible heat flow using a polynomial expression containing the heating rate in at least one term.

11. A method for analyzing a material comprising the steps of:
  (a) providing a power compensation differential scanning calorimeter having a sample position and a reference position, means for controlling the flow of heat to the sample position and means for controlling the flow of heat to the reference position;
  (b) selecting an underlying heating rate;
  (c) selecting a modulation function characterized by a modulation frequency and a modulation amplitude;
  (d) placing a sample of the material on the sample position of the power compensation differential scanning calorimeter and placing a reference material on the reference position of the power compensation differential scanning calorimeter;
  (e) controlling the flow of heat to the sample position and the flow of heat to the reference position such that:
    (i) the average difference between the temperature of the sample position and the temperature of the reference position is driven to zero,
    (ii) the flow of heat to the sample position includes an oscillating heat flow component, said component oscillating at the selected modulation frequency and modulation amplitude, and
    (iii) the average temperature of the sample position increases at the selected heating rate;
  (f) recording a differential signal representative of the average differential flow of heat to the sample position with respect to the reference position; and
  (g) deconvoluting the differential signal representative of the average differential flow of heat to the sample position with respect to the reference position to compute at least one deconvoluted signal.

12. The method of claim 11, wherein the step of deconvoluting the differential signal representative of the average differential flow of heat comprises deconvoluting the differential signal representative of the average differential flow of heat to the sample position with respect to the reference position into rapidly reversible and non-rapidly reversible components.

13. The method of claim 12, further comprising the step of controlling the underlying heating rate according to the rapidly reversible component.

14. The method of claim 12, further comprising the step of controlling the underlying heating rate according to the non-rapidly reversible component.

15. The method of claim 12, wherein the modulation function is a sinusoidal function.

16. The method of claim 12, wherein the modulation function is selected from the group of modulation functions consisting of square waves, sawtooth waves, triangular waves, pulse waves, polynomial waves and combinations thereof.

17. The method of claim 12, wherein the modulation function is selected to improve the separation between the rapidly reversible and non-rapidly reversible signals.

18. The method of claim 11, wherein the step of deconvoluting the differential signal representative of the average differential flow of heat comprises deconvoluting the differential signal representative of the average differential flow of heat to the sample position with respect to the reference position into rapidly reversible and non-rapidly reversible components using a discrete Fourier transform.

19. The method of claim 12, wherein the step of deconvoluting the differential signal representative of the average differential flow of heat comprises deconvoluting the differential signal representative of the average differential flow of heat to the sample position with respect to the reference position into rapidly reversible and non-rapidly reversible components using a polynomial expression containing the heating rate in at least one term.

20. A method for analyzing a material comprising the steps of:
  (a) providing a heat flux differential scanning calorimeter having a sample position;
  (b) selecting an underlying heating rate;
  (c) selecting a modulation function characterized by a modulation frequency and a modulation amplitude;
  (d) placing a reference material at the sample position;
  (e) varying the temperature of the sample position at the selected underlying heating rate;
  (f) recording a reference signal representative of the heat flow to the sample position;
  (g) placing a sample of the material on the sample position of the differential scanning calorimeter;
  (h) varying the temperature of the sample position such that the average temperature of the sample position increases at the underlying heating rate, and applying an oscillating heat flow to the sample position, said heat flow oscillating according to the selected modulation function;
  (i) recording a differential signal representative of the average differential total heat flow to the sample position compared to the reference signal, and recording the average temperature of the sample position; and
  (j) deconvoluting the differential signal representative of the average differential heat flow to the sample position compared to the reference signal to compute at least one deconvoluted signal.

21. The method of claim 21, wherein the step of deconvoluting the differential signal representative of the average differential heat flow comprises deconvoluting the differential signal representative of the average differential heat flow to the sample position compared to the reference signal into rapidly reversible and non-rapidly reversible components.

22. The method of claim 21, wherein the modulation function is a sinusoidal function.

23. The method of claim 21, wherein the modulation function is selected from the group of modulation functions consisting of square waves, sawtooth waves, triangular waves, pulse waves, polynomial waves and combinations thereof.

24. The method of claim 21, wherein the modulation function is selected to improve the separation between the rapidly reversible and non-rapidly reversible signals.

25. The method of claim 20, wherein the step of deconvoluting the differential signal representative of the average differential heat flow comprises deconvoluting the differential signal representative of the average differential heat flow to the sample position compared to the reference signal into rapidly reversible and non-rapidly reversible components using a discrete Fourier transform.

26. The method of claim 20, wherein the step of deconvoluting the differential signal representative of the average differential heat flow comprises deconvoluting the differential signal representative of the average differential heat flow to the sample position compared to the reference position into rapidly reversible and non-rapidly reversible components using a polynomial expression containing the heating rate in at least one term.

27. A method for analyzing a material comprising the steps of:
   (a) providing a power compensation differential scanning calorimeter having a sample position, means for controlling the flow of heat to the sample position, means for recording signals representative of the flow of heat to the sample position and means for recording the temperature of the sample position;
   (b) selecting an underlying heating rate;
   (c) selecting a modulation function characterized by a modulation frequency and a modulation amplitude;
   (d) placing a reference material at the sample position of the power compensation differential scanning calorimeter;
   (e) controlling the flow of heat to the sample position such that the temperature of the sample position increases at the selected heating rate;
   (f) recording a reference signal representative of the flow of heat to the sample position and recording a signal representative of the temperature of the sample position;
   (g) placing a sample of the material at the sample position of the power compensation differential scanning calorimeter;
   (h) controlling the flow of heat to the sample position such that:
      (i) the temperature of the sample position, on the average, increases at the underlying heating rate, and
      (ii) the flow of heat to the sample position includes an oscillating heat flow component, said component oscillating at the selected modulation frequency and modulation amplitude;
   (i) recording a differential signal representative of the average differential flow of heat to the sample position with respect to the reference signal, and recording the average sample temperature and
   (j) deconvoluting the differential signal representative of the average differential flow of heat to the sample position with respect to the reference signal to compute at least one deconvoluted signal.

28. The method of claim 27, wherein the step of deconvoluting the differential signal representative of the average differential flow of heat comprises deconvoluting the differential signal representative of the average differential flow of heat to the sample position with respect to the reference signal into rapidly reversible and non-rapidly reversible components.

29. The method of claim 28, further comprising the step of controlling the underlying heating rate according to the rapidly reversible component of the differential signal representative of the average differential heat flow.

30. The method of claim 28, wherein the modulation function is selected to improve the separation between the rapidly reversible and non-rapidly reversible signals.

31. The method of claim 27, wherein the step of deconvoluting the differential signal representative of the average differential flow of heat comprises deconvoluting the differential signal representative of the average differential flow of heat to the sample position with respect to the reference signal into rapidly reversible and non-rapidly reversible components using a discrete Fourier transform.

32. The method of claim 27, wherein the step of deconvoluting the differential signal representative of the average differential flow of heat comprises deconvoluting the differential signal representative of the average differential flow of heat to the sample position with respect to the reference signal into rapidly reversible and non-rapidly reversible components using a polynomial expression containing the heating rate in at least one term.

33. A differential scanning calorimeter comprising:
   (a) a sample position and a reference position;
   (b) means for selecting an underlying heating rate;
   (c) means for controlling the temperature of the reference position at the underlying heating rate;
   (d) means for selecting a modulation function characterized by a modulation frequency and a modulation amplitude;
   (e) means for varying the temperature of the sample position such that the average temperature of the sample position increases at the underlying heating rate;
   (f) means for applying an oscillating heat flow to the sample position, said heat flow oscillating according to the selected modulation function;
   (g) means for varying the temperature of the reference position at the selected underlying heating rate;
   (h) means for measuring the temperature of the sample position;
   (i) means for measuring a differential signal representative of the total heat flow to the sample position with respect to the reference position; and
   (j) means for deconvoluting the differential signal representative of the total heat flow to the sample position with respect to the reference position to compute at least one deconvoluted signal.

34. The differential scanning calorimeter of claim 33, wherein the means for deconvoluting the differential signal representative of the total heat flow comprises means for deconvoluting the differential signal representative of the total heat flow to the sample position with respect to the reference position into rapidly reversible and non-rapidly reversible components.

35. The differential scanning calorimeter of claim 34, further comprising means for controlling the underlying heating rate according to the rapidly reversible component of the differential signal representative of the total heat flow.

36. The differential scanning calorimeter of claim 34, further comprising means for controlling the underlying heating rate according to the non-rapidly reversible component of the differential signal representative of the total heat flow.

37. The differential scanning calorimeter of claim 33, wherein the means for deconvoluting the differential signal representative of the total heat flow comprises means for deconvoluting the differential signal representative of the total heat flow to the sample position with respect to the reference position into rapidly reversible and non-rapidly reversible components using a discrete Fourier transform.

38. A differential scanning calorimeter comprising:
(a) a sample position and a reference position;
(b) means for controlling the flow of heat to the sample position and means for controlling the flow of heat to the reference position;
(c) means for selecting an underlying heating rate;
(d) means for selecting a modulation function characterized by a modulation frequency and a modulation amplitude;
(e) means for controlling the flow of heat to the sample position and the flow of heat to the reference position such that:
  (i) the average difference between the temperature of the sample position and the temperature of the reference position is driven to zero,
  (ii) the flow of heat to the sample position includes an oscillating heat flow component, said component oscillating at the selected modulation frequency and modulation amplitude, and
  (iii) the average temperature of the sample position increases at the selected heating rate;
(g) means for recording a differential signal representative of the average differential flow of heat to the sample position with respect to the reference position; and
(h) means for deconvoluting the differential signal representative of the average differential flow of heat to the sample position with respect to the reference position to compute at least one deconvoluted signal.

39. The differential scanning calorimeter of claim 38, wherein the means for deconvoluting the differential signal representative of the average differential flow of heat comprises means for deconvoluting the differential signal representative of the average differential flow of heat to the sample position with respect to the reference position into rapidly reversible and non-rapidly reversible components.

40. The differential scanning calorimeter of claim 39, further comprising means for controlling the underlying heating rate according to the rapidly reversible component of the differential signal representative of the average differential flow of heat.

41. The differential scanning calorimeter of claim 39, further comprising means for controlling the underlying heating rate according to the non-rapidly reversible component of the differential signal representative of the average differential flow of heat.

42. The differential scanning calorimeter of claim 38, wherein the means for deconvoluting the differential signal representative of the average differential flow of heat comprises means for deconvoluting the differential signal representative of the average differential flow of heat to the sample position with respect to the reference position into rapidly reversible and non-rapidly reversible components using a discrete Fourier transform.

43. A differential scanning calorimeter comprising:
(a) a sample position;
(b) means for selecting an underlying heating rate;
(c) means for selecting a modulation function characterized by a modulation frequency and a modulation amplitude;
(e) means for varying the temperature of the sample position at the selected underlying heating rate;
(f) means for recording a reference signal representative of the heat flow to the sample position;
(h) means for varying the temperature of the sample position at the selected underlying heating rate modulated by the selected modulation function;
(i) means for recording a differential signal representative of the average differential heat flow to the sample position compared to the reference signal, and for recording the average temperature of the sample position; and
(j) means for deconvoluting the differential signal representative of the average differential heat flow to the sample position compared to the reference signal to compute at least one deconvoluted signal.

44. The differential scanning calorimeter of claim 43, wherein the means for deconvoluting the differential signal representative of the average differential heat flow comprises means for deconvoluting the differential signal representative of the average differential heat flow to the sample position compared to the reference signal into rapidly reversible and non-rapidly reversible components.

45. The differential scanning calorimeter of claim 51, wherein the means for deconvoluting the differential signal representative of the average differential heat flow comprises means for adjusting the modulation function according to the deconvoluted signal.

46. The differential scanning calorimeter of claim 44, further comprising means for controlling the underlying heating rate according to the non-rapidly reversible component of the differential signal representative of the average differential heat flow.

47. The differential scanning calorimeter of claim 43, wherein the means for deconvoluting the differential signal representative of the average differential heat flow comprises means for deconvoluting the differential signal representative of the temperature difference between the sample position and the reference position into rapidly reversible and non-rapidly reversible components using a discrete Fourier transform.

48. A differential scanning calorimeter comprising:
(a) a sample position;
(b) means for recording signals representative of the flow of heat to the sample position and for recording the temperature of the sample position;
(c) means for selecting an underlying heating rate;
(d) means for selecting a modulation function characterized by a modulation frequency and a modulation amplitude;
(e) means for controlling the flow of heat to the sample position such that the temperature of the sample position increases at the selected heating rate;

(f) means for recording a reference signal representative of the flow of heat to the sample position and for recording a signal representative of the temperature of the sample position;

(g) means for controlling the flow of heat to the sample position such that:
  (i) the temperature of the sample position, on the average, increases at the underlying heating rate, and
  (ii) the flow of heat to the sample position includes an oscillating heat flow component, said component oscillating at the selected modulation frequency and modulation amplitude;

(i) means for recording a differential signal representative of the average differential flow of heat to the sample position with respect to the reference signal, and for recording the average sample temperature; and (j) means for deconvoluting the differential signal representative of the average differential flow of heat to the sample position with respect to the reference position to compute at least one deconvoluted signal.

49. The differential scanning calorimeter of claim 48, wherein the means for deconvoluting the differential signal representative of the average differential flow of heat comprises means for deconvoluting the differential signal representative of the average differential flow of heat to the sample position with respect to the reference signal into rapidly reversible and non-rapidly reversible components.

50. The differential scanning calorimeter of claim 49, further comprising means for controlling the underlying heating rate according to the rapidly reversible component of the differential signal representative of the average differential flow of heat.

51. The differential scanning calorimeter of claim 49, further comprising means for controlling the underlying heating rate according to the non-rapidly reversible component of the differential signal representative of the average differential flow of heat.

52. The differential scanning calorimeter of claim 48, wherein the means for deconvoluting the differential signal representative of the average differential flow of heat comprises means for deconvoluting the differential signal representative of the average differential flow of heat to the sample position with respect to the reference signal into rapidly reversible and non-rapidly reversible components using a discrete Fourier transform.

53. A method for analyzing a material comprising the steps of:
  (a) providing a heat flux differential scanning calorimeter having a sample position and a reference position, said differential scanning calorimeter having means for measuring the differential heat flow to the sample position with respect to the reference position;
  (b) selecting an underlying heating rate;
  (c) selecting a modulation function characterized by a modulation frequency and a modulation amplitude;
  (d) placing a sample of the material on the sample position of the differential scanning calorimeter and placing a reference material on the reference position of the differential scanning calorimeter;
  (e) varying the temperature of the sample position such that the average temperature of the sample position increases at the underlying heating rate, and applying an oscillating temperature to the sample position, said temperature oscillating according to the selected modulation function;
  (f) varying the temperature of the reference position at the selected underlying heating rate;
  (g) measuring the temperature of the sample position and measuring a differential signal representative of the total heat flow to the sample position with respect to the reference position;
  (h) storing the differential signal representative of the total heat flow as total heat flow data, said total heat flow data forming a total heat flow data set;
  (i) separating the dependence of the total heat flow data set on temperature into at least one component data set; and
  (j) plotting said at least one component data set on an output device.

54. The method of claim 53, wherein said output device is a digital plotter.

55. The method of claim 53, wherein said output device is a display device.

56. The method of claim 53, wherein the at least one component data set is the rapidly reversible component of the total heat flow data set.

57. The method of claim 56, further comprising separating the dependence of the total heat flow data on temperature into a non-rapidly reversible component data set.

58. A method for analyzing a material comprising the steps of:
  (a) providing a power compensation differential scanning calorimeter having a sample position and a reference position, means for controlling the flow of heat to the sample position and means for controlling the flow of heat to the reference position;
  (b) selecting an underlying heating rate;
  (c) selecting a modulation function characterized by a modulation frequency and a modulation amplitude;
  (d) placing a sample of the material on the sample position of the power compensation differential scanning calorimeter and placing a reference material on the reference position of the power compensation differential scanning calorimeter;
  (e) controlling the flow of heat to the sample position and the flow of heat to the reference position such that:
    (i) the average difference between the temperature of the sample position and the temperature of the reference position is driven to zero,
    (ii) the flow of heat to the sample position includes an oscillating heat flow component, said component oscillating at the selected modulation frequency and modulation amplitude, and
    (iii) the average temperature of the sample position increases at the selected heating rate;
  (f) recording a differential signal representative of the average differential flow of heat to the sample position with respect to the reference position;
  (g) storing the differential signal representative of the average differential flow of heat as average heat flow data, said average heat flow data forming an average heat flow data set;
  (h) separating the dependence of the average heat flow data set on temperature into at least one component data set; and
  (i) plotting said at least one component data set on an output device.

59. The method of claim 58, wherein said output device is a digital plotter.

60. The method of claim 58, wherein said output device is a display device.

61. The method of claim 58, wherein the at least one component data set is the rapidly reversible component of the average heat flow data set.

62. The method of claim 61, further comprising separating the dependence of the average heat flow data on temperature into a non-rapidly reversible component data set.

63. A differential scanning calorimeter comprising:
(a) a sample position and a reference position;
(b) means for selecting an underlying heating rate;
(c) means for controlling the temperature of the reference position at the underlying heating rate;
(d) means for selecting a modulation function characterized by a modulation frequency and a modulation amplitude;
(e) means for varying the temperature of the sample position such that the average temperature of the sample position increases at the underlying heating rate;
(f) means for applying an oscillating heat flow to the sample position, said heat flow oscillating according to the selected modulation function;
(g) means for varying the temperature of the reference position at the selected underlying heating rate;
(h) means for measuring the temperature of the sample position;
(i) means for measuring a differential signal representative of the total heat flow to the sample position with respect to the reference position.
(j) means for storing the differential signal representative of the total heat flow as total heat flow data, said total heat flow data forming a total heat flow data set;
(h) means for separating the dependence of the total heat flow data set on temperature into at least one component data set; and
(i) means for plotting said at least one component data set on an output device.

64. The differential scanning calorimeter of claim 63, wherein said output device is a digital plotter.

65. The differential scanning calorimeter of claim 63, wherein said output device is a display device.

66. The differential scanning calorimeter of claim 63, wherein the at least one component data set is the rapidly reversible component of the total heat flow data set.

67. The differential scanning calorimeter of claim 66, further comprising means for separating the dependence of the total heat flow data on temperature into a non-rapidly reversible component data set.

68. A differential scanning calorimeter comprising:
(a) a sample position and a reference position;
(b) means for controlling the flow of heat to the sample position and means for controlling the flow of heat to the reference position;
(c) means for selecting an underlying heating rate;
(d) means for selecting a modulation function characterized by a modulation frequency and a modulation amplitude;
(e) means for controlling the flow of heat to the sample position and the flow of heat to the reference position such that:
(i) the average difference between the temperature of the sample position and the temperature of the reference position is driven to zero,
(ii) the flow of heat to the sample position includes an oscillating heat flow component, said component oscillating at the selected modulation frequency and modulation amplitude, and
(iii) the average temperature of the sample position increases at the selected heating rate;
(g) means for recording a differential signal representative of the average differential flow of heat to the sample position with respect to the reference position;
(h) means for storing the differential signal representative of the average differential flow of heat as average heat flow data, said average heat flow data forming an average heat flow data set;
(i) means for separating the dependence of the average heat flow data set on temperature into at least one component data set; and
(i) means for plotting said at least one component data set on an output device.

69. The differential scanning calorimeter of claim 68, wherein said output device is a digital plotter.

70. The differential scanning calorimeter of claim 68, wherein said output device is a display device.

71. The differential scanning calorimeter of claim 68, wherein the at least one component data set is the rapidly reversible component of the average heat flow data set.

72. The differential scanning calorimeter of claim 71, further comprising means for separating the dependence of the average heat flow data on temperature into a non-rapidly reversible component data set.

73. A method for analyzing a material using a differential scanning calorimeter comprising the steps of:
(a) selecting an underlying heating rate, modulation frequency and modulation amplitude;
(b) placing a sample of the material in the differential scanning calorimeter;
(c) varying the temperature of the sample in the differential scanning calorimeter according to the selected underlying heating rate, the selected modulation frequency and the selected modulation amplitude;
(d) recording a signal representative of differential changes in the heat flow to and from the sample;
(e) storing the differential signal representative of the heat flow as heat flow data, said heat flow data forming a heat flow data set;
(i) separating the dependence of the heat flow data set on temperature into at least one component data set; and
(j) plotting said at least one component data set on an output device.

74. The method of claim 73, wherein said output device is a digital plotter.

75. The method of claim 73, wherein said output device is a display device.

76. The method of claim 73, wherein the at least one component data set is the rapidly reversible component of the heat flow data set.

77. The method of claim 76, further comprising separating the dependence of the total heat flow data on temperature into a non-rapidly reversible component data set.

78. A differential scanning calorimeter comprising:
(a) means for varying the temperature of a sample in the differential scanning calorimeter according to an underlying heating rate;

(b) means for selecting a modulation frequency and a modulation amplitude;

(c) means for controlling the temperature of the sample according to the selected underlying heating rate, modulation frequency and modulation amplitude;

(d) means for detecting the heat flow to and from the sample with respect to a reference as a function of temperature, as the temperature is varied according to the heating rate, the modulation frequency, and the modulation amplitude;

(e) means for recording a signal representative of differential changes in the heat flow to and from the sample;

(f) means for storing the differential signal representative of the heat flow as heat flow data, said heat flow data forming a heat flow data set;

(g) means for separating the dependence of the heat flow data set on temperature into at least one component data set; and (h) means for plotting said at least one component data set on an output device.

79. The differential scanning calorimeter of claim 78, wherein said output device is a digital plotter.

80. The differential scanning calorimeter of claim 78, wherein said output device is a display device.

81. The differential scanning calorimeter of claim 78, wherein the at least one component data set is the rapidly reversible component of the heat flow data set.

82. The differential scanning calorimeter of claim 81, further comprising means for separating the dependence of the heat flow data on temperature into a non-rapidly reversible component data set.

83. A differential thermal analyzer comprising:
(a) means for varying the temperature of a sample in the differential thermal analyzer according to an underlying heating rate;
(b) means for selecting a modulation frequency and a modulation amplitude;
(c) means for controlling the temperature of the sample according to the selected underlying heating rate, modulation frequency and modulation amplitude;
(d) means for detecting the heat flow to and from the sample with respect to a reference as a function of temperature, as the temperature is varied according to the heating rate, the modulation frequency, and the modulation amplitude;
(e) means for recording a signal representative of differential changes in the heat flow to and from the sample;
(f) means for storing the differential signal representative of the heat flow as heat flow data, said heat flow data forming a heat flow data set;
(g) means for separating the dependence of the heat flow data set on temperature into at least one component data set; and
(h) means for plotting said at least one component data set on an output device.

84. The differential thermal analyzer of claim 83, wherein said output device is a digital plotter.

85. The differential thermal analyzer of claim 83, wherein said output device is a display device.

86. The differential thermal analyzer of claim 83, wherein the at least one component data set is the rapidly reversible component of the heat flow data set.

87. The differential thermal analyzer of claim 86, further comprising means for separating the dependence of the heat flow data on temperature into a non-rapidly reversible component data set.

88. A differential scanning calorimeter comprising:
(a) a sample position and a reference position;
(b) means for controlling the flow of heat to the sample position and means for controlling the flow of heat to the reference position;
(c) means for selecting an underlying heating rate;
(d) means for selecting a modulation function characterized by a modulation frequency and a modulation amplitude;
(e) means for controlling the flow of heat to the sample position and the flow of heat to the reference position such that:
  (i) the average difference between the temperature of the sample position and the temperature of the reference position is driven to zero,
  (ii) the flow of heat to the sample position and to the reference position includes an oscillating heat flow component, said component oscillating at the selected modulation frequency and modulation amplitude, and
  (iii) the average temperature of the sample position and the reference position increases at the selected heating rate;
(g) means for recording a differential signal representative of the average differential flow of heat to the sample position with respect to the reference position;
(h) means for storing the differential signal representative of the average differential flow of heat as average heat flow data, said average heat flow data forming an average heat flow data set;
(i) means for separating the dependence of the average heat flow data set on temperature into at least one component data set; and
(i) means for plotting said at least one component data set on an output device.

89. The differential scanning calorimeter of claim 88, wherein said output device is a digital plotter.

90. The differential scanning calorimeter of claim 88, wherein said output device is a display device.

91. The differential scanning calorimeter of claim 88, wherein the at least one component data set is the rapidly reversible component of the average heat flow data set.

92. The differential scanning calorimeter of claim 91, further comprising means for separating the dependence of the average heat flow data on temperature into a non-rapidly reversible component data set.

* * * * *

US005439291C1

(12) REEXAMINATION CERTIFICATE (4556th)
United States Patent
Reading

(10) Number: US 5,439,291 C1
(45) Certificate Issued: Apr. 16, 2002

(54) METHOD AND APPARATUS FOR AC DIFFERENTIAL THERMAL ANALYSIS

(75) Inventor: Michael Reading, London (GB)

(73) Assignee: TA Instruments, Inc., New Castle, DE (US)

Reexamination Request:
No. 90/005,518, Oct. 12, 1999

Reexamination Certificate for:
Patent No.: 5,439,291
Issued: Aug. 8, 1995
Appl. No.: 08/171,656
Filed: Dec. 22, 1993

(*) Notice: This patent is subject to a terminal disclaimer.

Related U.S. Application Data

(63) Continuation-in-part of application No. 08/060,214, filed on May 7, 1993, now Pat. No. 5,346,306, which is a continuation of application No. 07/844,448, filed on Mar. 2, 1992, now Pat. No. 5,224,775.

(51) Int. Cl.⁷ .............................................. G01N 25/00
(52) U.S. Cl. .............................. 374/11; 374/33; 374/43
(58) Field of Search .............................. 374/10, 11, 12, 374/13, 14, 16, 31, 33, 43

(56) References Cited

U.S. PATENT DOCUMENTS 5,080,495 A  1/1992 Hashimoto et al.

OTHER PUBLICATIONS

Physical Review Letters, First–Order Transition in Chromium at the Neel Temperature, P.R. Garnier and M.B. Salamon, Oct. 13, 1971, pp. 1523–1526.

Computerized Equipment for Measuring the Amplitude and Phase of ULF Harmonic Signals, Plenum Publishing Corporation, 1987, pp. 763–767.

S.C. Mraw and D.F. Naas, "The Measurement of Accurate Heat Capacities By Differential Scanning Calorimetry: Comparison of d.s.c. Results of Pyrite (100 to 800 K) with Literature Values from Precision Adiabatic Calorimetry," J. Chem. Thermodynamics, vol. 11, 1979, pp. 567–584.

P. Claudy, J.C. Commercon, and J.M. Letoffe, "Quasi–Study of the Glass Transition of Glycerol by DSC," Thermochimica Acta, vol. 128, Aug. 1988, pp. 251–260.

A. Maesono and R. Kato, translation into English of a Japanese article, "Recently Developed Instruments Relevant to ac Calorimetry." (no date).

H. Albert, "Pulsed–Current Control and Measurement System for Precision Microcalorimetry," The Review of Scientific Instruments, vol. 43, No. 5, 1972, pp. 766–774.

J. Zynger, "Automated, Stepping Differential Calorimeter for the Analysis of Purity," Analytical Chemistry, vol. 47, No. 8, Jul. 1975, pp. 1380–1384.

(List continued on next page.)

Primary Examiner—G. Bradley Bennett

(57) ABSTRACT

The present invention is a modulated differential thermal analysis technique for determining the composition, phase, structure, identification, or other properties of a material that undergoes a transition as function of temperature or other driving variable. As applied to differential scanning calorimetric analysis (DSC), the preferred embodiment comprises (1) heating a sample of the material with a linear temperature ramp that is modulated with a sinusoidal heating rate oscillation; (2) simultaneously heating a reference at the same linear temperature ramp; (3) measuring the differential temperature of the sample and reference; and (4) deconvoluting the resultant heat flow signal into rapidly and non-rapidly reversible components.

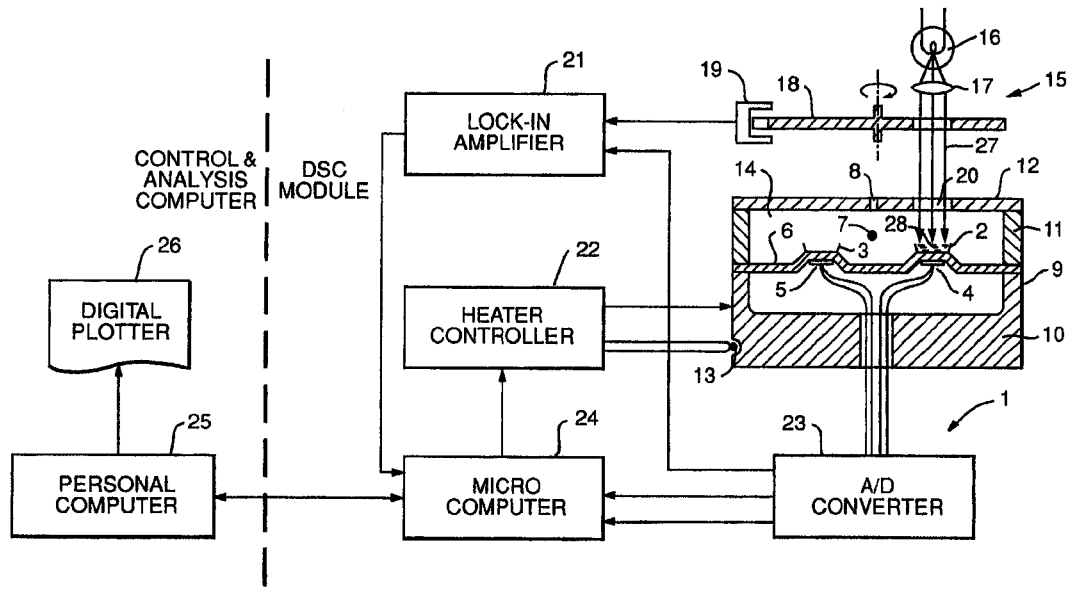

OTHER PUBLICATIONS

T. Sturgill, R. Johnson, and R. Biltonen, "Thermal Perturbation Techniques in Characterizing Ligand–Macromolecule Interactions: Theory and Application to the Proflavin–a–Chymotrypsin System," Biopolymers, vol. 17, 1978, pp. 1773–1792.

P. Privalov, "Scanning Microcalormeters for Studying Macromolecules," Pure & Appl. Chem., vol. 52, 1980, pp. 479–497.

C. Festa and N. Ceccanti, "A Differntial Calorimeter for Measuring Heats of Solution With a Pulse Time Modulation System," Societa Chimica Italiana, 1980, pp. 431–437.

W. Van Osdol, R. Biltonen, and M. Johnson, "Measuring the Kinetics of Membrane Phase Transitions," Journal of Biochemical and Biophysical Methods, vol. 20, 1989, pp. 1–46.

J. Rouquerol, "Controlled Transformation Rate Thermal Analysis: The Hidden Face of Thermal Analysis," Thermochimica Acta, 144, 1989, pp. 209–224.

D. Cahill, "Thermal Conductivity Measurement from 30 to 750 K the 3u Method," Rev. Sci. Instrum. vol. 62, Feb. 1990, pp. 802–808.

D. Bertolini, M. Cassettari, G. Salvetti, E. Tombari, and S. Veronesi, "A Differential Calorimetric Technique for Heat Capacity and Thermal Conductivity Measurement of Liquids," Rev. Sci. Instrum., vol. 61, No. 9, Sep. 1990, pp. 2416–2419.

A.M. Cocero and J.L. Kokini, "The Study of the Glass Transition of Glutenin Using Small Amplitude Oscillatory Rheological Measurements and Differential Scanning Calorimetry," The Society of Rheology, Inc. vol. 35, No. 2, Feb. 1991, pp. 257–270.

M. Barrio, J. Font, J. Montasell, and J. Ll. Tamarit, "AC Calorimetry Applied To Powdered Samples, Simulation and Tests," Journal of Thermal Analysis, vol. 37, 1991, pp. 39–52.

Y. Saruyama, "AC Calorimetry at the First Order Phase Transition Point," Journal of Thermal Analysis, vol. 38, 1992, pp. 1827–1833.

Y.A. Kraftmakher, "Modulation Calorimetry," Institute of Inorganic Chemistry, pp. 591–641. (no date).

M. Straume and E. Freire, "Two–Dimensional Differential Scanning Calorimetry: Simultaneous Revolution of Intrinsic Protein Structural Energetic And Ligand Binding Interactions by Global Linkage Analysis," Analytical Biochemistry, 203, 1992, pp. 259–268.

C.W. Garland, "High–Resolution AC Calorimetry and Critical Behavior at Phase Transitions," Thermochimica Acta 88 (1985) pp. 127–142.

M. Meichle and C.W. Garland, "Calorimetric study of the smectic–A—smectic–C phase transition in liquid crystals," Physical Review A, 27 (5), May, 1983, pp. 2624–2631.

G. Sanchez, M. Meichle and C.W. Garland, "Critical heat capacity in a 3–methylpentane+nitroethane mixture near its consolute point," Physical Review A, 28(8), Sep., 1983.

S. Ikeda and Y. Ishikawa, "Improvement of AC Calorimetry," Japanese Journal of Applied Physics, 18 (7), Jul. 1979, pp. 1367–1372.

S. Imaizumi, T. Matsuda, and I. Hatta, "Measurement of Dynamic Specific Heat Capacity of Lysozome Crystals," Journal of the Physical Society of Japan, 47 (5), Nov., 1979.

J. Ohsawa, T. Nishinaga and S. Uchiyama, "Measurement of the Specific Heat of Boron Monophosphide by AC Calorimetry," Japanese Journal of Applied Physics, 17 (6), Jun., 1978.

J.E. Smaardyk and J.M. Mochel, "High resolution ac calorimeter for organic liquids," Review of Scientific Instruments 49 (7), Jul. 1978, pp. 988–993.

"Complex Plane Analysis of Heat Capacity of Polymers in the Glass Transition Region," by H. Gobrecht et al., Journal of Physics E: Scientific Instruments, 1971, vol. 4, pp. 21–23.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–92 is confirmed.

\* \* \* \* \*